United States Patent [19]

Hignett et al.

[11] 4,200,592

[45] Apr. 29, 1980

[54] CATALYTIC HYDROFORMYLATION

[75] Inventors: Rosemary R. Hignett, Reading; Peter J. Davidson, Woodcote, both of England

[73] Assignee: Johnson, Matthey & Co., Limited, London, England

[21] Appl. No.: 916,535

[22] Filed: Jun. 19, 1978

[30] Foreign Application Priority Data

Jun. 21, 1977 [GB] United Kingdom ............... 25857/77
Aug. 19, 1977 [GB] United Kingdom ............... 34920/77

[51] Int. Cl.$^2$ ............................................. C07C 45/10
[52] U.S. Cl. ............................................. 260/604 HF
[58] Field of Search ............... 260/604 HF; 252/431 P

[56] References Cited

U.S. PATENT DOCUMENTS

| 3,378,590 | 4/1968 | Usami et al. ................ 260/604 HF |
| 3,631,111 | 12/1971 | Tucci .............................. 260/604 |

FOREIGN PATENT DOCUMENTS 1338225 11/1973 United Kingdom ............. 260/604 HF

*Primary Examiner*—Werren B. Lone
*Attorney, Agent, or Firm*—Cushman, Darby & Cushman

[57] ABSTRACT

This invention relates to catalytic hydroformylation reactions, for example the hydroformylation of internal olefins. In particular the invention relates to a process for the production of a straight chain aldehyde from an olefin comprising reacting the said olefin in a liquid reaction medium with hydrogen and carbon monoxide at a total pressure of less than 500 psig in the presence of a complex of Rh(I) in solution in the said medium and a homogeneous co-catalyst dissolved in said reaction medium comprising a co-ordination complex of a transition metal other than rhodium selected from Group 6 or Group 8 of the Periodic Table.

The transition metal is, preferably, selected from the group consisting of Cr, Mo, W, Fe, Co, Pd, Pt and Ru.

24 Claims, No Drawings

CATALYTIC HYDROFORMYLATION

This invention relates to catalytic hydroformylation reactions; more particularly it relates to the catalytic hydroformylation of internal olefins.

Catalysts frequently used in the hydroformylation of terminal olefins are complexes of Rh(1) with triphenylphosphine. Examples are Hrh(CO) (PPh$_3$)$_2$, Hrh(CO) (PPh$_3$)$_3$ and (PPh$_3$) Rh(CO) (acac). These catalysts can be used in solutions in which an excess of triphenylphosphine is present. Using catalysts of this type is now possible to obtain usefully high normal/iso aldehyde ratios at moderate total pressure in the gaseous phase when working with terminal olefins. One process by which such catalysts can be used to obtain high normal yields of aldehyde is described in U.S. Pat. No. 4,108,905 and the equivalent British Pat. No. 1338225 dated 16th Dec. 1970.

When working with internal olefins however the straight chain product cannot be obtained unless isomerisation in one form or another occurs prior to or during the hydroformylation reaction. It is an object of the present invention to produce normal or straight-chain aldehydes from internal olefins by a process also operating at moderate total pressures in the gaseous phase, said process also comprising a hydroformylation reaction. By "moderate total pressures" we mean pressures less than about 500 psig and more preferably less than about 200 psig. At such lower pressures the economics of the process are considerably enhanced.

According to one aspect of the present invention a process for the production of a straight chain aldehyde from an olefin comprises reacting the said olefin in a liquid reaction medium with hydrogen and carbon monoxide at a total pressure less than 500 psig in the presence of a complex of Rh(I) in solution in the said medium and a homogeneous co-catalyst dissolved in said reaction medium comprising a co-ordination complex of a transition metal selected from Group 6 or Group 8 of the Periodic Table.

As co-catalysts we particularly prefer to use co-ordination complexes of Cr, Mo, W, Fe, Co, Pd, Pt and Ru. We find it useful to use complexes formed by organic or carbon-containing ligands such as CO acetylacetone CH$_3$COCH$_2$COCH$_3$ and triphenylphosphine.

We have found that there is a trade off between rate of reaction and high n/iso ratio. At high rates of reaction the n/iso ratio achieved is lower and at lower rate of reaction a usefully high n/iso ratio is obtained. We have also found that either the rate of reaction or the n/iso ratio can be improved (but generally not both) by increasing the molar ratio of co-catalyst to rhodium above 1:1. In some cases ratios of 25:1 and 100:1 have achieved distinct improvements in the desired direction as regards rate or product isomer ratio.

According to a second aspect of the present invention, therefore, a process for the production of a straight chain aldehyde from an olefin comprises reacting the said olefin in a liquid reaction medium with hydrogen and carbon monoxide at a total pressure less than 500 psig in the presence of a complex of Rh(I) in solution in the said medium and a homogeneous co-catalyst dissolved in said reaction medium comprising a co-ordination complex of a transition metal selected from Group 6 or Group 8 of the Periodic Table and in which the molar ratio of co-catalyst complex present to Rh(I) complex present is greater than 1:1.

The preferred range for the said molar ratio is from 2:1 to 100:1.

According to a third aspect of the present invention a process for the production of a straight chain aldehyde from an olefin comprises reacting the said olefin in a liquid reaction medium with hydrogen and carbon monoxide at a total pressure of less than 500 psig in the presence of a complex of Rh(I) in solution in the said medium and a homogeneous co-catalyst dissolved in the said reaction medium comprising a compound selected from the group consisting of Pd(acac)$_2$, (PhCN)$_2$PdCl$_2$, Mo(CO)$_6$, Fe$_2$(CO)$_9$, Co$_2$(CO)$_8$, Cr(CO)$_6$, Ru$_3$(CO)$_{12}$, W(CO)$_6$, Pt(PPh$_3$)$_4$ and Pd(PPh$_3$)$_4$.

Of the above-mentioned co-catalyst we particularly prefer Cr(CO)$_6$, Mo(CO)$_6$ and Ru$_3$(CO)$_{12}$. This reaction is most successfully used with short chain internal olefins and is suitable for use with 2-pentene, 2- and 3-hexenes and 2-butene. We prefer to use the olefin itself as the reaction medium. Hydrogen and carbon monoxide are added in gaseous form under pressure but dissolve in the rapidly stirred reaction medium. Suitable partial pressures for hydrogen and carbon monoxide are between 0.5 and 5.0 atmospheres. We prefer to use 1 atm. CO and 3 atm. H$_2$. Suitable temperatures are between 80° and 140° C. We prefer to operate in the region 100° C.-135° C.

The complex of Rh(I) is preferably a complex containing a stabilising donor ligand.

Generally speaking suitable donor ligands for stabilisation purposes are organic compounds having in the molecule a phosphorus atom, such atom being in a valency state such that it possesses a lone pair of electrons. This valency state is normally three. Preferred ligands are often, therefore, tertiary organic phosphines or phosphites:

in which R$^1$, R$^2$ and R$^3$ may be the same or different and may be hydrogen, aryl or alkyl, aralkyl, arlkaryl or substituted alkyl, aryl alkaryl or alkaryl groups.

Conveniently, at least one of the stabilising donor ligands is a phosphorus compound having organic substituents, the phosphorus atom having a valency state possessing a lone pair of electrons. The substituents may be alkyl, aryl, aralkyl, aryloxy, alkoxy, hydroxy, halogeno, amino, amido or nitro groups. Tri-aryl substituted phosphines such as triphenyl phosphine, trinaphthylphosphine and tri-para tolylphosphine are often preferred. The phosphorus compound may be a tri-aryl substituted phosphite, e.g. triphenyl phosphite.

Stabilising donor ligands which may be used in this invention are often described as "biphyllic ligands". By "biphyllic ligand" is meant a compound having an element with a pair of electrons capable of forming a co-ordinate bond with a metal atom and simultaneously having the ability to accept electrons from the metal, thereby providing additional stability to the resulting complex. The term "biphyllic ligand" has been more fully defined by R. G. Pearson in Journal of the American Chemical Society, Volume 82, page 787 (1960).

The stabilising donor ligand which may be used in this invention may be a polydentate compound. This means that it may contain more than one atom which co-ordinates to the central metal atom or ion. In this invention, a stabilising donor ligand or biphyllic ligand might contain more than one phosphorus atom, for example.

The complex hydridocarbonyl tris (triphenyl phosphine) rhodium(I) is stable and can be isolated. We prefer to prepare this complex separately and add it to the reaction medium before commencement of the reaction.

However, we have also found that under the conditions of the reaction, complex rhodium catalysts for use in the process according to the invention may be generated in situ in a number of different ways. For example, if the stabilising donor ligand is a tertiary organo phosphine, complex hydrido carbonyl rhodium complexes suitable for use in the present invention may be generated in situ from such compounds such as:

RhX(CO)(PR$_3$)$_3$ or

RhX(CO)(PR$_2$)$_2$ or

RHX$_3$(PR$_3$)$_3$ where R is as stated above for R$^1$, R$^2$ and R$^3$ and X is either halogen or pseudo-halogen. With these halogen or halogen-type complexes, an inhibition period is observed before the hydroformylation begins. We have also found that in the presence of acceptors for hydrogen halide, e.g. an organic base such as triethylamine, this inhibition period disappears. A further possibility is therefore the inclusion of a compound such as an organic base which can act as a hydrogen halide acceptor in the raction medium. Alternatively, the reaction medium itself may act as an acceptor.

Hydrido carbonyl complexes of rhodium which may be used in this invention may also be generated in other ways, e.g. from rhodium compounds in other oxidation states; The rhodium can be added as a simple trivalent salt, e.g. RhCl$_3$, a rhodium carbonyl, e.g. Rh$_6$(CO)$_{16}$, a rhodium II carboxylate Rh$_2$(COOR)$_4$ e.g. Rhodium (II) acetate, a rhodium (I) carbonyl carboxylate e.g. [Rh(CO)$_2$CH$_2$COO]$_2$, a rhodium oxide, rhodium sesquioxide Rh$_2$O$_3$, a rhodium (III) β diketonate such as rhodium acetonylacetonate or a rhodium (I) carbonyl β diketonate, e.g. Rh(CO)$_2$(Acac) where Acac is acetyl acetonate.

Particularly useful rhodium complexes which may be used as catalysts in the invention are (Ph=phenyl):

RhH(CO)(PPh$_3$)$_3$

RhH(CO)(PPh$_3$)$_2$

RhH(CO)$_2$(PPh$_3$)$_2$

Other useful hydrido carbonyl complexes of rhodium are

RhH(CO)[P(OPh)$_3$]$_3$

RhH(CO)[P(OPh)$_3$]$_2$

RhH(CO)$_2$[P(OPh)$_3$]$_2$

It has been found to be useful to have a stoichiometric excess of stabilizing donor ligand present in the reaction medium over and above that necessary to form the complex of Rh(I). We have in this invention found it useful to have a ligand: Rh catalyst ratio greater than 1:1 up to about 500:1. Where PPh$_3$ is the ligand used a useful ratio is 200:1.

EXAMPLE 1

Using an Mo(CO)$_6$ co-catalyst; Rh:Mo=1:1 molar and 500 ppm Rh in a 2-butene substrate we have obtained a 100% increase in rate of reaction. Rh complex used: HRh(CO)(PPh$_3$)$_3$. The autoclave is charged with H$_2$ and CO at a ratio 3:1. P$_{CO}$ at operating temperature (130° C.) is 1 atm. [PPh$_3$]:[Rh]=200:1.

| n/iso | 1.6:1 without catalyst | with catalyst |
|---|---|---|
| Rate (Arbitrary pressure decrement units) | 0.16 | 0.33 |

EXAMPLES 2-10

Rh(I) catalyst was used in the form (PPh$_3$)$_3$Rh(CO)H in which [Rh]=500 ppm and an excess of triphenyl phosphine is present such that [PPh$_3$]:[Rh]=200:1. The autoclave is charged with 1 atmosphere CO and 3 atmospheres H$_2$ and topped up with a 1:1 [H$_2$]:[CO] mixture. The temperature is maintained at 130° C. The total pressure was always within the range 100–200 psig. The rate is measured by cumulative timing of arbitrary pressure decrement units from 7.5 to 7 atm. The substrate solvent consisted of an excess of 2- and 3-hexenes (present in weight ratio 60:40). The normal/iso isomer ratio of C$_7$ aldehyde (heptanal) was measured by vapour phase chromatography using a 5 ft. column having an OD of 0.25 inches packed with 10% SE 30 on Chomosorb W and operated at 75° C.

The rates of reaction and n/iso ratios achieved for different molar ratios of co-catalyst to rhodium in the production of n and iso heptanal are as shown in Table 1. (The first result is a control experiment which was checked by repetition.)

Table 1

| Example | Co-catalyst | Molar ratio | Rate (Arbitrary pressure decrement units) | C$_7$ aldehyde (n/iso ratio) |
|---|---|---|---|---|
| | None(Rh only) | — | 0.16 | 1.6 (control experiment) |
| 2 | Mo(CO)$_6$ | Rh : Mo | | |
| | | 1 : 1 | 0.17 | 2.0 |
| | | 1 : 2 | 0.24 | 1.7 |
| | | 1 : 25 | 0.25 | 1.6 |
| | | 1 : 100 | 0.55 | 1.3 |
| 3 | Co$_2$(CO)$_8$ | Rh : Co | | |
| | | 1 : 3 | 0.21 | 1.6 |

Table 1-continued

| Example | Co-catalyst | Molar ratio | Rate (Arbitrary pressure decrement units) | C₇ aldehyde (n/iso ratio) |
|---|---|---|---|---|
| 4 | Cr(CO)₆ | Rh : Cr | | |
| | | 1 : 20 | 0.14 | 1.8 |
| | | 1 : 1 | 0.16 | 1.6 |
| | | 1 : 2 | 0.09 | 1.9 |
| 5 | Ru₃(CO)₁₂ | Rh : Ru | | |
| | | 1 : 25 | 0.39 | 1.8 |
| | | 1 : 1 | 0.31 | 2.0 |
| | | 1 : 2 | 0.19 | 1.5 |
| | | 1 : 2 | 0.22 | 1.5 (repeated) |
| | | 1 : 5 | 0.23 | 1.4 |
| 6 | W(CO)₆ | Rh : W | | |
| | | 1 : 1 | 0.17 | 1.7 |
| | | 1 : 25 | 0.22 | 1.7 |
| 7 | Fe₂(CO)₉ | Rh : Fe | | |
| | | 1 : 4 | 0.16 | 1.6 |
| | | 1 : 25 | 0.23 | 1.6 |
| 8 | Pt(PPh₃)₄ | Rh : Pt | | |
| | | 1 : 1 | 0.23 | 1.6 |
| 9 | Pd(acac)₂ | Rh : Pd | | |
| | | 1 : 1 | 0.21 | 1.9 |
| 10 | Pd(PPh₃)₄ | 1 : 2 | slow | 2.7 |

The results indicate considerably enchanced rate and n/iso ratio at low total pressure of reaction in the presence of the indicated co-catalyst. In practically every instance an improved rate of reaction or yield of normal product isomer is obtained by increasing the molar ratio of co-catalyst complex present to Rh(I) complex present.

EXAMPLES 11–12 (comparative)

These examples are added to demonstrate the ineffectiveness of co-catalysts derived from transition metals selected from Group 7 of the Periodic Table. The co-catalysts were tested under the same conditions as those described for the tests in Examples 2–10 above. No improvement with either Re or Mn is observed.

| Example | Co-catalyst | Molar Ratio | Rate | C₇aldehyde (n/iso ratio) |
|---|---|---|---|---|
| 11 | Re₂(CO)₁₀ | Rh : Re | | |
| | | 1 : 1 | 0.16 | 1.6 |
| | | 1 : 25 | 0.16 | 1.6 |
| 12 | Mn₂(CO)₁₀ | Rh : Mn | | |
| | | 1 : 25 | 0.16 | 1.6 |

We claim:

1. A process for the production of a straight chain aldehyde from an internal olefin selected from the group consisting of 2-pentene, 2-hexene, 3-hexene and 2-butene which comprises reacting the said olefin at a temperature between 80° and 140° C. in a liquid reaction medium with hydrogen and carbon monoxide at a total pressure of at least 1 atmosphere and less than 500 psig in the presence of an hydrido carbonyl complex of Rh(I) including a triaryl phosphite or triaryl phosphine stabilizing donor ligand, said complex being in solution in the said medium and a homogeneous co-catalyst also dissolved in said reaction medium comprising a co-ordination compound selected from the group consisting of Pd(acac)₂, (PhCN)₂PdCl₂, Mo(CO)₆, Fe₂(CO)₉, Co₂(CO)₈, Cr(CO)₆, Ru₃(CO)₁₂, W(CO)₆, Pt(PPh₃)₄ and Pd(PPh₃)₄, the molar ratio of co-catalyst complex present to Rh(I) complex present being greater than 1:1.

2. A process according to claim 1 in which the molar ratio is within the range 2:1 to 100:1.

3. A process according to claim 1 in which the triaryl phosphite is triphenyl phosphite.

4. A process according to claim 1 wherein the triaryl phosphine is triphenyl phosphine.

5. A process according to claim 1 in which the hydrido carbonyl complex of rhodium is RhH(CO)(PPh₃)₃ or

RhH(CO)(PPh₃)₂.

6. A process according to claim 1 in which the hydrido carbonyl complex of rhodium is RhH(CO)[P(OPh)₃]₃ or

RhH(CO)[P(OPh)₃]₂.

7. A process according to claim 1 in which the hydrido carbonyl complex of rhodium is RhH(CO)₂(PPh₃)₂.

8. A process according to claim 1 in which the hydrido carbonyl complex of rhodium is RhH(CO)₂[P(OPh)₃]₂.

9. A process according to claim 1 wherein the hydrido carbonyl complex is generated in situ.

10. A process according to claim 9 wherein the hydrido carbonyl complex is generated from RhX(CO)(PR₃)₃ or

RhX₃(PR₃)₃ or

RhX(CO)(PR₃)₂ where X is a halogen or pseudo-halogen and R is an alkyl, aryl, aralkyl, alkaryl, or substituted alkyl, aryl, aralkyl or alkaryl group.

11. A process according to claim 10 including an acceptor for hydrogen halide.

12. A process according to claim 11 wherein the acceptor is an organic base.

13. A process according to claim 12 wherein the organic base is triethylamine.

14. A process according to claim 13 wherein the acceptor is the phosphorus-containing stabilising donor ligand.

15. A process according to claim 9 in which the source of rhodium is a trivalent rhodium salt, a rhodium carbonyl, a rhodium (II) carboxylate, a rhodium (I) carbonyl carboxylate, a rhodium oxide, a rhodium (III) $\beta$-diketonate, or a rhodium carbonyl $\beta$ diketonate.

16. A process according to claim 15 wherein the rhodium carboxylate is the acetate.

17. A process according to claim 15 wherein the $\beta$-diketonate is acetylacetonate.

18. A process according to claim 1 wherein the molecular ratio of $H_2:CO$ is within the range 1:15 to 5:1.

19. A process according to claim 18 wherein the molecular ratio of $H_2:CO$ is within the range 5:1 to 1:6.

20. A process according to claim 18 which is carried out at a total pressure less than 200 psi.

21. A process according to claim 20 which is carried out at a temperature within the range 115° C.–140° C.

22. A process according to claim 21 wherein the temperature range is 120° C.–130° C.

23. A process according to claim 1 wherein the ligand/catalyst ratio lies within the range of 1:1 to 500:1.

24. A process according to claim 23 wherein the ligand/catalyst ratio is 200:1.